United States Patent
Brink et al.

(10) Patent No.: US 7,692,020 B2
(45) Date of Patent: Apr. 6, 2010

(54) PROCESS FOR THE PREPARATION OF PYRIDYLCARBOXYLIC AMIDES AND ESTERS

(75) Inventors: Monika Brink, Ingelheim (DE); Marcus Knell, Hochheim (DE); Jan Hendrik Wevers, Hohen-Sülzen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/092,021

(22) PCT Filed: Oct. 26, 2006

(86) PCT No.: PCT/EP2006/067818

§ 371 (c)(1),
(2), (4) Date: Apr. 29, 2008

(87) PCT Pub. No.: WO2007/051759

PCT Pub. Date: May 10, 2007

(65) Prior Publication Data

US 2008/0249313 A1    Oct. 9, 2008

Related U.S. Application Data

(60) Provisional application No. 60/733,755, filed on Nov. 7, 2005.

(51) Int. Cl.
*C07D 213/81* (2006.01)

(52) U.S. Cl. ................. 546/323; 546/291; 546/298; 546/314; 546/327

(58) Field of Classification Search ............... 546/290, 546/298, 300, 314, 326, 329, 334, 335, 336, 546/341, 345, 291, 323, 327
See application file for complete search history.

(56) References Cited

U.S. PATENT DOCUMENTS 6,320,053 B1 * 11/2001 Knell et al. ............. 546/298

FOREIGN PATENT DOCUMENTS

| EP | 0 447 004 | 9/1991 |
| EP | 0 646 566 | 4/1995 |
| EP | 0 899 262 | 3/1999 |

OTHER PUBLICATIONS

Katritzky, A.R. et al., "Electrophilic Substitution of Heteroaromatic Compounds with Six-Membered Rings", Angew Chem. Inter. Edit., 1967, p. 608-615, vol. 6, No. 7.

* cited by examiner

*Primary Examiner*—Bernard Dentz
*Assistant Examiner*—David E Gallis
(74) *Attorney, Agent, or Firm*—Brinks Hofer Gilson & Lione

(57) ABSTRACT

The invention relates to a process for the preparation of pyridylcarboxylic amides and esters I, Formula (I) wherein Hal, X and $R^1$ have the meanings given in claim 1, which comprises the following steps: (a) heating a mixture consisting essentially of trichloromethylpyridine II, Formula (II), wherein Hal has the meaning given, and 1.0 to 1.5 equivalents of concentrated sulfuric acid, characterized in that the trichloromethylpyridine II in a liquid form is added to the concentrated sulfuric acid at a temperature from 110° C. to 160° C.; and (b) reacting the intermediate product obtained in step (a) with an amine or alcohol III, $HXR^1$, wherein X and $R^1$ have the meaning given, optionally in the presence of a solvent and/or a base.

16 Claims, No Drawings

PROCESS FOR THE PREPARATION OF PYRIDYLCARBOXYLIC AMIDES AND ESTERS

The present invention relates to a process for the preparation of pyridylcarboxylic amides and esters I

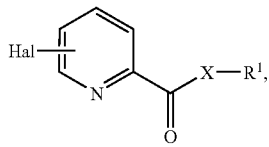

wherein
Hal represents a halogen atom;
represents O or $NR^2$;
$R^1$ represents a $C_1$-$C_6$-alkyl or aryl group, wherein both groups may be substituted by one or more halogen atoms, nitro, cyano, $C_1$-$C_6$-alkyl, $C_1$-$C_6$-haloalkyl or $C_1$-$C_6$-alkoxy groups;
$R^2$ represents a hydrogen atom or a $C_1$-$C_6$-alkyl group;

which comprises the following steps:
(a) heating a mixture consisting essentially of a trichloromethylpyridine II,

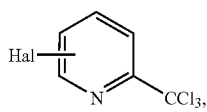

wherein Hal has the meaning given, and 1.0 to 1.5 equivalents of concentrated sulfuric acid,
characterized in that the trichloromethylpyridine II in a liquid form is added to the concentrated sulfuric acid at a temperature from 110 to 160° C.; and
(b) reacting the intermediate product obtained in step (a) with an amine or alcohol III, $$HXR^1 \qquad \qquad III,$$

wherein X and $R^1$ have the meaning given, optionally in the presence of a solvent and/or a base.

Another aspect of the present invention is a process for the preparation of (aryloxy)pyridylcarboxylic amides and esters IV

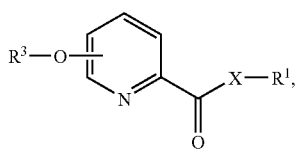

wherein $R^1$ and X have the meaning given, and
$R^3$ represents an aryl group, which may be substituted by one or more halogen atoms, nitro, cyano, $C_1$-$C_6$-alkyl, $C_1$-$C_6$-haloalkyl or $C_1$-$C_6$-alkoxy groups;

wherein the pyridylcarboxylic amides and esters I or a salt thereof are prepared from a trichloromethylpyridine II according to the present invention and (c) are further reacted with an aromatic alcohol V, $$R^3\text{—OH} \qquad \qquad V,$$

wherein $R^3$ has the meaning given,
optionally in the presence of a base.

Pyridylcarboxylic amides and esters I are suitable intermediates for the preparation of a broad variety of compounds which are useful as agrochemicals or pharmaceuticals. In particular, they are key intermediates in the preparation of herbicidal phenoxypyridylcarboxamides which are described for example in EP 0 447 004.

The European patent application EP 0 646 566 suggests to hydrolyze trichloromethyl heteroarenes with water in the presence of chlorinated hydrocarbons and a Lewis acid and to react the resulting heteroarylcarbonyl chloride with an amine.

However, this process causes problems with respect to the dosing rate and the exact equimolar dosing of water. Any excess of water will cause hydrolysis of the desired acid chloride compound and therefore reduce the yields. Moreover, in these days using chlorinated hydrocarbons is not desired because of environmental problems, and the amount of solvent used in the prior art procedure is high. Furthermore, the reaction time needed using water/1,2-dichloroethane is very long (24 h).

The European patent application EP 0 899 262 discloses a process for the preparation of pyridylcarboxylic amides and esters in which sulfuric acid is added to a pyridyltrichloromethane compound.

However, this process causes problems since the intermediate formed solidifies at temperatures below 100° C., but re-melting of this solidified intermediate is difficult due to decomposition under evolution of hydrochloric acid and sulphurtrioxide.

It is, therefore, an object of the present invention to provide an efficient new process for the preparation of pyridylcarboxylic amides and esters in high yield and purity.

The novel improved process avoids the disadvantages of the processes of the prior art and enables to carry out the production of pyridylcarboxamides and esters in technical scale and high yields using ready-available educts.

Moreover the process according to the present invention has several advantages with respect to process safety compared to the process disclosed by EP 0 899 262 A:

The mixture obtained in step (a) is not as sensitive to cooling during adding of the trichloromethypyridine II. The reaction mixture obtained during adding time is more stable and loss of heating would not cause solidification problems.

Furthermore, when the sulfuric acid is added to the trichloromethylpyridine II as disclosed by EP 0 899 262, the trichloromethylpyridine II shows the tendency to evaporate from the reaction mixture into the overhead system and is condensing and/or solidifying there. In addition to potential loss of yield, this may cause blockage of valves and vent lines representing a safety risk.

So the process of the present invention clearly reduces the evaporation of the richloromethylpyridine II.

Other objects and advantages of the present invention will be apparent to those skilled in the art from the following description and the appended claims.

In general terms, unless otherwise stated herein, the term "the trichloromethylpyridine of formula II in a liquid form" includes trichloromethylpyridines II, which are liquid at room temperature; and trichloromethylpyridines II, which are solid at room temperature but are utilized either in form of a solution in an inert solvent or at a temperature above their melting point, i.e. they are used in molten form.

In general terms, unless otherwise stated herein, the term "pyridylcarboxylic amides I" stands for "pyridylcarboxylic amides and esters I, wherein X represents $NR^2$".

In general terms, unless otherwise stated herein, the term "pyridylcarboxylic esters I" stands for "pyridylcarboxylic amides and esters I, wherein X represents O".

In general terms, unless otherwise stated herein, the term "amine III" stands for "amine or alcohol III, wherein X represents $NR^2$".

In general terms, unless otherwise stated herein, the term "alcohol III" stands for "amine or alcohol III, wherein X represents O".

In general terms, unless otherwise stated herein, the term "(aryloxy)pyridylcarboxylic amides IV" stands for "(aryloxy)pyridylcarboxylic amides and esters IV, wherein X represents $NR^2$".

In general terms, unless otherwise stated herein, the term "(aryloxy)pyridylcarboxylic esters IV" stands for "(aryloxy)pyridylcarboxylic amides and esters IV, wherein X represents O".

The organic moieties mentioned in the definition of the substituents $R^1$, $R^2$ and $R^3$ or as substituents on phenyl, naphthyl or anthranyl rings are—like the term halogen—collective terms for individual enumerations of the individual group members. All hydrocarbon chains, i.e. all alkyl, haloalkyl and alkoxy groups can be straight-chain or branched, the prefix $C_n$-$C_m$ denoting in each case the possible number of carbon atoms in the group. Halogenated substituents preferably carry one, two, three, four or five identical or different halogen atoms. The term halogen denotes in each case fluorine, chlorine, bromine or iodine.

Examples of other meanings are:

$C_1$-$C_4$-alkyl: $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, i.e., for example, $CH_2F$, $CHF_2$, $CF_3$, $CH_2Cl$, dichloromethyl, trichloromethyl, chlorofluoromethyl, dichlorofluoromethyl, chlorodifluoromethyl, 2-fluoroethyl, 2-chloroethyl, 2-brom-oethyl, 2-iodoethyl, 2,2-difluoroethyl, 2,2,2-trifluoroethyl, 2-chloro-2-fluor-oethyl, 2-chloro-2,2-difluoroethyl, 2,2-dichloro-2-fluoroethyl, 2,2,2-tri-chloroethyl, $C_2F_5$, 2-fluoropropyl, 3-fluoropropyl, 2,2-difluoropropyl, 2,3-difluoro-propyl, 2-chloro-propyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoro-propyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$-$C_6$-haloalkyl: a $C_1$-$C_4$-haloalkyl radical as mentioned above and also, for example, 5-fluoropentyl, 5-chloropentyl, 5-bromopentyl, 5-iodopentyl, undeca-fluoropentyl, 6-fluorohexyl, 6-chlorohexyl, 6-bromohexyl, 6-iodohexyl and dodecafluorohexyl;

$C_1$-$C_4$-alkoxy: for example $OCH_3$, $OC_2H_5$, n-propoxy, $OCH(CH_3)_2$, n-butoxy, $OCH(CH_3)$—$C_2H_5$, $OCH_2$—$CH(CH_3)_2$ or $OC(CH_3)_3$, preferably $OCH_3$, $OC_2H_5$ or $OCH(CH_3)_2$;

$C_1$-$C_6$-alkoxy: a $C_1$-$C_4$-alkoxy radical as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

aryl: a mono-, bi- or tricyclic aromatic carbocycle containing 6 to 14 ring members, for example phenyl, naphthyl und anthracenyl;

As a rule aromatic groups are preferred, which are substituted by at least one electron-withdrawing group, in particular by one or more halogen atoms, nitro, cyano or $C_1$-$C_6$-haloalkyl groups.

In a particular embodiment of the process according to the present invention the radicals of the compounds according the present invention are as defined below, these definitions being both on their own and in combination with one another, particular embodiments of the present invention:

Preference is given to a process according to the present invention wherein

Hal represents fluorine, chlorine or bromine;
preferably chlorine or bromine;
particular preferably chlorine.

Preference is also given to a process according to the present invention wherein
X represents oxygen.

Preference is also given to a process according to the present invention wherein
X represents $NR^2$.

Preference is also given to a process according to the present invention wherein
$R^1$ represents $C_1$-$C_6$-alkyl, which may be substituted by one or more halogen atoms, nitro, cyano, $C_1$-$C_6$-alkyl, $C_1$-$C_6$-haloalkyl or $C_1$-$C_6$-alkoxy groups;
preferably $C_1$-$C_6$-alkyl, which may be substituted by one or more halogen atoms;
particularly preferably $C_1$-$C_6$-alkyl;
very particularly preferably $C_1$-$C_4$-alkyl.

Preference is also given to a process according to the present invention wherein
$R^1$ represents an aryl group, which may be substituted by one or more halogen atoms, nitro, cyano, $C_1$-$C_6$-alkyl, $C_1$-$C_6$-haloalkyl or $C_1$-$C_6$-alkoxy groups;
preferably a phenyl group, which may be substituted by one or more halogen atoms, nitro, cyano, $C_1$-$C_6$-alkyl, $C_1$-$C_6$-haloalkyl or $C_1$-$C_6$-alkoxy groups;
particularly preferably a phenyl group, which may be substituted by one or two halogen atoms selected from fluorine and chlorine;

very particular preferably a phenyl group, which may be substituted by one halogen atom;

especially preferably a phenyl group, which may be substituted by one fluorine atom.

Preference is also given to a process according to the present invention wherein
$R^2$ represents hydrogen.

Preference is also given to a process according to the present invention wherein
$R^2$ represents $C_1$-$C_6$-alkyl;
preferably $C_1$-$C_4$-alkyl.

Preference is also given to a process according to the present invention wherein
X represents O; and
$R^1$ represents $C_1$-$C_6$-alkyl, which may be substituted by one or more halogen atoms, nitro, cyano, $C_1$-$C_6$-alkyl, $C_1$-$C_6$-haloalkyl or $C_1$-$C_6$-alkoxy groups;
preferably $C_1$-$C_6$-alkyl, which may be substituted by one or more halogen atoms;
particularly preferably $C_1$-$C_6$-alkyl;
very particularly preferably $C_1$-$C_4$-alkyl;
most preferably isopropyl.

Preference is also given to a process according to the present invention wherein
X represents $NR^2$;
$R^1$ represents an aryl group, which is substituted by one or more halogen atoms, nitro, cyano, $C_1$-$C_6$-alkyl, $C_1$-$C_6$-haloalkyl or $C_1$-$C_6$-alkoxy groups;
preferably a phenyl group, which is substituted by one or more halogen atoms, nitro, cyano, $C_1$-$C_6$-alkyl, $C_1$-$C_6$-haloalkyl or $C_1$-$C_6$-alkoxy groups;
particularly preferably a phenyl group, which is substituted by one or two halogen atoms and/or $C_1$-$C_6$-haloalkyl groups;
very particular preferably a phenyl group, which may be substituted by one or two halogen atoms selected from fluorine and chlorine;
very particular preferably a phenyl group, which may be substituted by one halogen atom;
especially preferably a phenyl group, which may be substituted by one fluorine atom; and
$R^2$ represents hydrogen.

Preference is also given to a process according to the present invention wherein
$R^3$ represents an aryl group, which may be substituted by one or two halogen atoms or $C_1$-$C_6$-haloalkyl groups;
preferably an aryl group, which may be substituted by one $C_1$-$C_6$-haloalkyl group.

Preference is also given to a process according to the present invention wherein
$R^3$ represents a phenyl group, which may be substituted by one or more halogen atoms, nitro, cyano, $C_1$-$C_6$-alkyl, $C_1$-$C_6$-haloalkyl or $C_1$-$C_6$-alkoxy groups;
preferably a phenyl group, which may be substituted by one or more halogen atoms or $C_1$-$C_6$-haloalkyl groups;
particularly preferably a phenyl group, which may be substituted by a $C_1$-$C_6$-haloalkyl group;
very particularly preferably a phenyl group, which may be substituted by a $C_1$-$C_6$-haloalkyl group in 3-position of the phenyl moiety;
especially preferably a phenyl group, which may be substituted by a $C_1$-$C_4$— haloalkyl group in 3-position of the phenyl moiety.

Preference is also given to a process according to the present invention wherein the trichloromethylpyridines II are substituted by one halogen atom,
preferably by a chlorine atom.

Particular preference is given to a process according to the present invention wherein the trichloromethylpyridines II are represented by trichloromethylpyridines IIA

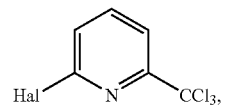

IIA wherein Hal represents a halogen atom;
preferably fluorine, chlorine or bromine;
particularly preferably chlorine or bromine;
especially preferably chlorine.

Most preference is given a process according to the present invention wherein the trichloromethylpyridines II are represented by nitrapyrin (NP), a compound IIA, wherein Hal is Cl.

Step (a) of the process according to the present invention comprises heating a mixture consisting essentially of a trichloromethylpyridine II and 1.0 to 1.5 equivalents of concentrated sulfuric acid, characterized in that the trichloromethylpyridine II in a liquid form is added to the concentrated sulfuric acid at a temperature from 110 to 160° C.:

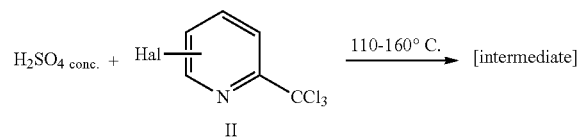

The intermediate product formed in step (a) comprises a compound of formula VI and/or formula VII, or a structural isomeric form thereof:

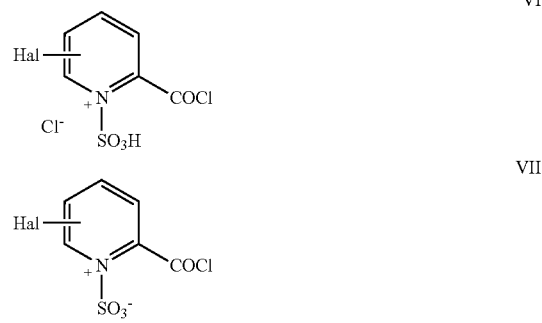

The reaction of the trichloromethylpyridine II with the sulfuric acid is carried out from 110° C. to 160° C., preferably from 120° C. to 150° C., most preferred at 135° C.

Preference is given to a process according to the present invention wherein in step (a) the mixture of the trichloromethylpyridine II and the concentrated sulfuric acid is kept at temperatures from 120 to 150° C. for 30 to 300 minutes, more preferably for 30 to 240 minutes.

Step (a) can be carried out under reduced or elevated pressure, preferably it is carried out at ambient pressure.

Step (a) can be carried out in an inert organic solvent with a suitable boiling point or in the absence of any solvent.

Suitable solvents are aliphatic hydrocarbons such as mixtures of $C_5$-$C_8$-alkanes, aromatic hydrocarbons such as toluene, o-, m- and p-xylene, and halogenated hydrocarbons such as chlorobenzene.

It is also possible to use mixtures of the solvents mentioned.

Preference is given to a process according to the present invention wherein step (a) is carried out in the absence of any solvent.

Preference is given to a process according to the present invention wherein in step (a) the concentrated sulfuric acid contains less than 3% by weight of water.

Step (a) is carried out in the presence of 1.0 to 1.5 equivalents, preferably of 1.1 to 1.4 equivalents, particularly preferably of 1.25 to 1.35 equivalents of concentrated sulfuric acid.

Preference is given to a process according to the present invention wherein in step (a) the trichloromethylpyridine II is added slowly, more preferably added in a time range of 1 to 5 hours to the concentrated sulfuric acid.

Under these preferred reaction conditions the reaction of step (a) is as a rule completed within 30 to 300 minutes, preferably within 45 to 240 minutes, in particular within 60 to 210 minutes.

The trichloromethylpyridines II required are commercially available or can be prepared by halogenation of 2-trichloromethylpyridine (e.g. A. R. Katritzky, C. D. Johnson, Angew. Chem. Int. Ed. 1967, 6, 608-615).

Step (b) of the process according to the present invention comprises reacting the intermediate product obtained in step (a) with an amine or alcohol III optionally in the presence of an inert solvent and/or a base:

[intermediate] + HXR$^1$ ⟶ Hal—[pyridine ring]—C(=O)—X—R$^1$

III

I

The reaction of the intermediate product obtained in step (a) with an amine or alcohol III is usually carried out at a temperature between ambient temperature and the reflux temperature of the reaction mixture, preferably at from 0° C. to 140° C., particularly preferably at from 20° C. to 120° C., most preferred at 40° C. to 100° C. in the presence of an inert solvent and/or a base.

As a rule step (b) can be carried out under reduced or elevated pressure, preferably it is carried out at ambient pressure.

Step (b) of the reaction according to the invention may be carried out in the absence or presence of a solvent, which promotes the reaction or at least does not interfere with it.

Suitable solvents are apolar solvents including aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, chloroform, 1,2-dichloroethane and chlorobenzene, nitroalkanes such as nitroethane.

It is also possible to use mixtures of the solvents mentioned.

Step (b) of the reaction according to the invention may be carried out in the absence or presence of a base.

Suitable bases are, in general, organic bases, e.g. tertiary amines such as tri($C_1$-$C_6$-alkyl)amines (e.g. trimethylamine, triethylamine, diisopropylethylamine), N-methylpiperidine, pyridine, substituted pyridines such as collidine, lutidine, N-methylmorpholine and 4-dimethylaminopyridine and also bicyclic amines.

The bases are generally employed in equimolar amounts, in excess or, if appropriate, they can be used as solvent. Preferably the bases are used in equimolar amounts.

In general, the intermediate product obtained in step (a) and the amine or alcohol III are used in equimolar amounts.

It might be advantageous to employ an excess of III based on the intermediate product.

The resulting intermediate product obtained in step (a) is preferably reacted with the amine or alcohol III in a liquid form or upon dilution with an inert solvent.

In a preferred embodiment the intermediate product of step (a), preferably in a liquid form, is transferred to the amine or alcohol III.

The reaction of step (b) with an alcohol III is preferably carried out from 40° C. to 70° C., most preferred at 65° C.

In the event that the intermediate product formed in step (a) is reacted with an alcohol III, step (b) is preferably carried out with an excess of said alcohol.

Preferably the intermediate product formed in step (a) is reacted with an alcohol III as a solvent.

Alternatively, the intermediate product obtained in step (a) may be treated with an alcohol III in the presence of an inert solvent such as toluene.

Preference is given to a process according to the present invention wherein in step (b) the intermediate product obtained in step (a) is treated with an alcohol III wherein
$R^1$ represents $C_1$-$C_6$-alkyl, which may be substituted by one or more halogen atoms,
nitro, cyano, $C_1$-$C_6$-alkyl, $C_1$-$C_6$-haloalkyl or $C_1$-$C_6$-alkoxy groups;
preferably $C_1$-$C_6$-alkyl;
more preferably ethyl or isopropyl.

The reaction of step (b) with an amine III is preferably carried out from 50° C. to 140° C., most preferred at 80° C.

In the event that the intermediate product formed in step (a) is reacted with an amine III, step (b) is preferably carried out in the presence of a base as listed above; particularly preferably in the presence of tri($C_1$-$C_6$-alkyl)amines (e.g. trimethylamine, triethylamine, diisopropylethylamine), N-methylpiperidine, pyridine, substituted pyridines such as collidine, lutidine, N-methylmorpholine and 4-dimethylaminopyridine; very particular preferably tri($C_1$-$C_6$-alkyl)amines; especially preferably triethylamine.

Preferably the intermediate product formed in step (a) is reacted with an amine III as a solvent.

Alternatively, the intermediate product obtained in step (a) may be treated with an amine III in the presence of an inert solvent, preferably an aromatic hydrocarbon such as toluene.

Preference is given to a process according to the present invention wherein the intermediate product obtained in step (a) is treated with an amine III in the presence of a base and an aromatic hydrocarbon as a solvent.

Preference is also given to a process according to the present invention wherein the intermediate product obtained in step (a) is treated with an amine III wherein
$R^1$ represents a phenyl group, which is substituted by one or two halogen atoms and/or $C_1$-$C_6$-haloalkyl groups;
preferably a phenyl group, which may be substituted by one or two halogen atoms selected from fluorine and chlorine;
particular preferably a phenyl group, which may be substituted by one halogen atom;

especially preferably a phenyl group, which may be substituted by one fluorine atom; and R² represents hydrogen.

Under this preferred reaction conditions step (b) is as a rule completed within 0.5 to 5, in particular 1 to 4 hours.

The amines or alcohols III required are commercially available.

The obtained pyridylcarboxylic amides and esters I may be purified by standard procedures, as for example by crystallization or chromatography, in particular by crystallization.

However, since the pyridylcarboxylic amides and esters I are obtained in high purity with the process according to the invention, it is also possible to use the obtained product without further purification to prepare (aryloxy)pyridylcarboxylic amides and esters IV.

Pyridylcarboxylic amides I can also prepared from pyridylcarboxylic esters I,
which have been prepared in step (b) by treating the intermediate product obtained in step (a) with an alcohol III as mentioned above,
by treating the pyridylcarboxylic esters I with an amine III as hereinbefore defined, in the presence of a base:

Hal—[pyridine]—C(=O)—O—R¹  +  HNR²R¹  →
pyridylcarboxylic ester I        amine III Hal—[pyridine]—C(=O)—N(R²)R¹
pyridylcarboxylix amide I The reaction of the pyridylcarboxylic ester I with an amine III is usually carried out at a temperature between ambient temperature and the reflux temperature of the reaction mixture, preferably at from 25° C. to 140° C., particularly preferably at from 50° C. to 110° C., most preferred at 80° C. to 100° C. in the presence of an inert solvent and a base.

As a rule step (b) can be carried out under reduced or elevated pressure, preferably it is carried out at ambient pressure.

This reaction according to the invention may be carried out in the absence or presence of a solvent, which promotes the reaction or at least does not interfere with it.

Suitable solvents are apolar solvents including aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, chloroform, 1,2-dichloroethane and chlorobenzene.

Particular preference is given to aliphatic hydrocarbons, halogenated hydrocarbons and aromatic hydrocarbons.

It is also possible to use mixtures of the solvents mentioned.

Suitable bases are, in general Inorganic compounds such as alkali metal and alkaline earth metal hydroxides such as lithium hydroxide, sodium hydroxide, potassium hydroxide and calcium hydroxide, alkali metal and alkaline earth metal oxide such as lithium oxide, sodium oxide, calcium oxide and magnesium oxide, as well as alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Preferred bases are metal alkoxides such as sodium methoxide or sodium ethoxide.

The bases are generally employed in catalytic amounts, however they can also be employed in equimolar amounts, in excess or, if appropriate, be used as solvent.

In general, the pyridylcarboxylic ester I and the amine III are used in equimolar amounts. It might be advantageous to employ an excess of III based on the pyridylcarboxylic ester I.

Preference is given to a process according to the present invention wherein a pyridylcarboxylic ester I is treated with an amine III in the presence of a base as mentioned above and an aromatic hydrocarbon as solvent.

In the event that pyridylcarboxylic amides I are prepared from pyridylcarboxylic esters I by treating the pyridylcarboxylic esters I with an amine III,
wherein R² represents a hydrogen atom,
in the presence of a base,
salts of formula I.1 are formed:

Hal—[pyridine]—C(=N⁺HR¹)—O⁻     I.1

Preference is given to a process according to the present invention wherein a pyridylcarboxylic ester IA, Hal—[pyridine]—C(=O)—O—R¹     IA wherein R¹ represents a $C_1$-$C_6$-alkyl group;
preferably an isopropyl group, is reacted with an amine III, wherein R² represents a hydrogen atom, to give the salts I.1A Hal—[pyridine]—C(=N⁺HR¹)—O⁻     I.1A Another aspect of the present invention is a process for the preparation of (aryloxy)pyridylcarboxylic amides and esters IV

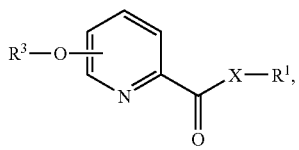

wherein

X represents O or $NR^2$;

$R^1$ represents a $C_1$-$C_6$-alkyl or aryl group, wherein both groups may be substituted by one or more halogen atoms, nitro, cyano, $C_1$-$C_6$-alkyl, $C_1$-$C_6$-haloalkyl or $C_1$-$C_6$-alkoxy groups;

$R^2$ represents a hydrogen atom or a $C_1$-$C_6$-alkyl group;

$R^3$ represents an aryl group, which may be substituted by one or more halogen atoms, nitro, cyano, $C_1$-$C_6$-alkyl, $C_1$-$C_6$-alkoxy or $C_1$-$C_6$-haloalkyl groups;

which comprises the following steps:

(a) heating a mixture consisting essentially of a trichloromethylpyridine II as hereinbefore defined, and 1.0 to 1.5 equivalents of concentrated sulfuric acid, characterized in that the trichloromethylpyridine II in a liquid form is added to the concentrated sulfuric acid at a temperature from 110 to 160° C.;

(b) reacting the intermediate product obtained in step (a) with an amine or alcohol III as hereinbefore defined, optionally in the presence of a solvent and/or a base; and (c) reacting the pyridylcarboxylic amides and esters I or a salt thereof obtained in step (b) with an aromatic alcohol V, $R^3$—OH  V, wherein $R^3$ has the meaning given;
optionally in the presence of a base:

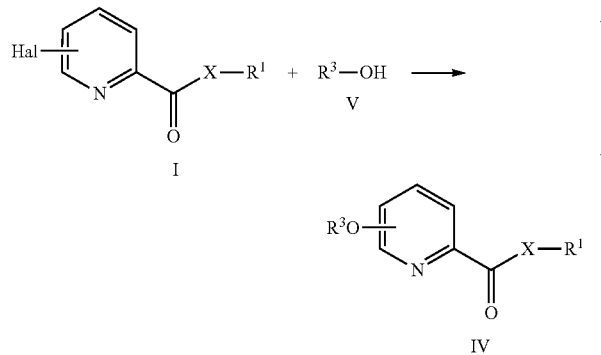

The reaction of the pyridylcarboxylic amides and esters I or a salt thereof with an aromatic alcohol V is usually carried out at from 0° C. to the boiling point of the reaction mixture, preferably at from 60° C. to 200° C., particularly preferably at from 140° C. to 180° C., in an inert organic solvent optionally in the presence of a base.

Suitable solvents are apolar solvents including aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichlorormethane, 1,2-dichlororethane, chloroform and chlorobenzene, as well as amides such as dimethylformamide, N,N-dimethylacetamide or N-methylpyrrolidone.

Particular preference is given to apolar or polar aprotic solvents like aliphatic hydrocarbons, halogenated hydrocarbons, aromatic hydrocarbons or amides such as dimethylformamide, N,N-dimethylacetamide or N-methylpyrrolidone or mixtures of any of these solvents.

It is also possible to use mixtures of the solvents mentioned.

Suitable bases are, in general Inorganic compounds such as alkali metal and alkaline earth metal hydroxides such as lithium hydroxide, sodium hydroxide, potassium hydroxide and calcium hydroxide, as well as alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Particular preference is given to metal alkoxides or metal hydroxides such as sodium methoxide, sodium ethoxide, sodium hydroxide or potassium hydroxide.

The bases are generally employed in equimolar amounts, however they can also be employed in excess or, if appropriate as solvent.

Preference is given to a process according to the present invention wherein in step (c) the pyridylcarboxylic amides and esters I or a salt thereof obtained according to the present invention are reacted with an aromatic alcohol V without further purification.

Preference is also given to a process according to the present invention wherein a pyridylcarboxylic ester IA is reacted with an aromatic alcohol V in the presence of a base to give (aryloxy)pyridylcarboxylic esters IVA:

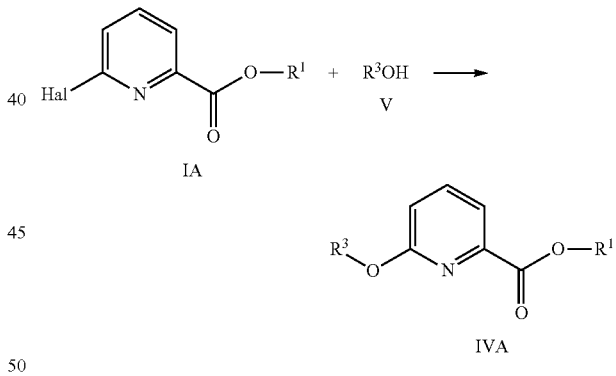

In a particularly preferred embodiment according to the present invention the liquid obtained in step (a) is added to 5 to 15 equivalents of an alcohol III, in particular isopropanol, at a temperature between 20 and 85° C.

The resulting reaction mixture is diluted with an aromatic hydrocarbon and washed with water.

The resulting solution is added at temperatures from 120 to 160° C. to a solution of the salt of an aromatic alcohol V, which is obtained by treating 1.01 to 1.30 equivalents, in particular about 1.22 equivalents, of an aromatic alcohol V, and a solution of sodium alkoxide, preferably 1.01 to 1.30 equivalents sodium alkoxide, in particular 1.22 equivalents sodium alkoxide, most preferred sodium methoxide,
in an alcohol;

in an aromatic hydrocarbon, in particular xylene, at 100-140° C.

Preferably the excess of the remained alcohol V is distilled off before the pyridylcarboxylic ester I is added to the solution of the salt of an aromatic alcohol V. The reaction mixture is as rule heated to 140-160° C. and kept at this temperature for 2-8 hours to complete the reaction.

In a preferred embodiment of the present invention a pyridylcarboxylic ester I or the salt I1 thereof obtained according to the present invention in step (b) is reacted with an aromatic alcohol V in the presence of a base [step (c)], and the resulting (aryloxy)pyridylcarboxylic ester IV is subsequently treated with an amine III [step (d)] to give (aryloxy) pyridylcarboxylic amides IV:

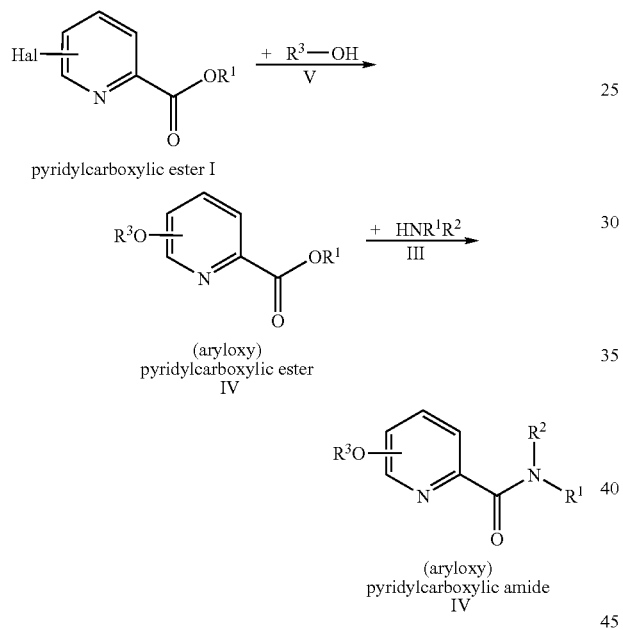

Particular preference is given to a process according to the present invention, wherein in step (c) a pyridylcarboxylic ester IA,

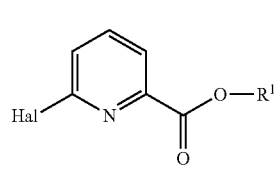

wherein $R^1$ represents a $C_1$-$C_6$-alkyl group;
preferably an isopropyl group, is reacted with an aromatic alcohol V in the presence of a base; and treating the resulting (aryloxy)pyridylcarboxylic ester IVA,

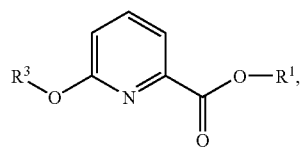

wherein $R^1$ and $R^3$ have the meaning given, with an amine III as hereinbefore defined in the presence of a base.

In a further preferred embodiment of the present invention a pyridylcarboxylic ester I is reacted with an amine III, wherein $R^2$ is hydrogen, and the resulting salts I.1 are subsequently treated with an aromatic alcohol V to give (aryloxy) pyridylcarboxylic amides IV wherein $R^2$ is hydrogen:

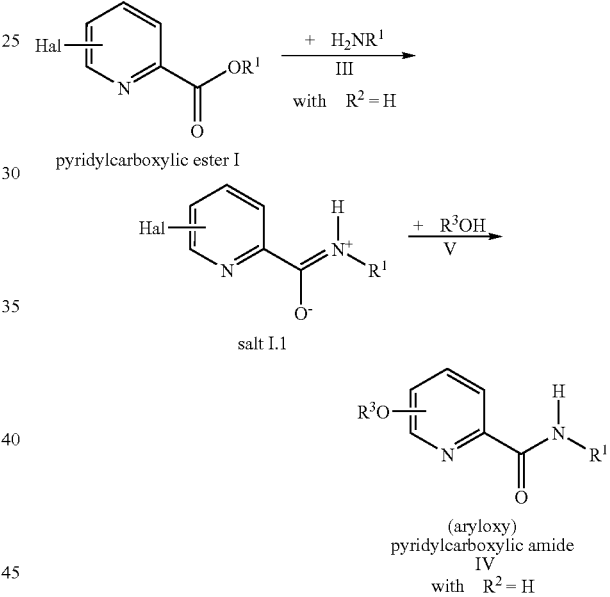

Particular preference is also given to a process according to the present invention wherein a pyridylcarboxylic ester IA,

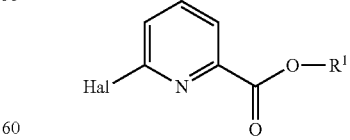

wherein $R^1$ represents a $C_1$-$C_6$-alkyl group;
preferably an isopropyl group, is reacted with an amine III, wherein $R^2$ represents a hydrogen atom, to give the salts I.1A

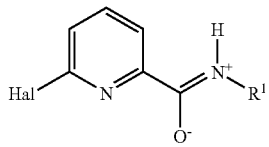

I.1A which are subsequently treated with an aromatic alcohol V to give the (aryloxy)pyridylcarboxylic amides IV.A wherein $R^2$ is hydrogen

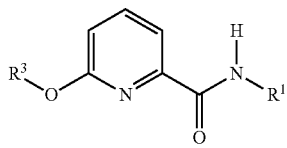

IVA without using any additional base.

In a further particularly preferred embodiment according to the present invention an amine III, in particular 0.9 to 1.2 equivalents, preferably a halogenated aniline, in particular 4-fluoroaniline is added to the resulting reaction mixture at 120-150° C., in particular at 135° C.;

optionally followed by adding a sodium alkoxide solution, in particular sodium methoxide solution, preferably catalytical amounts, more preferably 0.05 to 0.20 equivalents, mostly preferably about 0.13 equivalents in 10 to 60 minutes with simultaneous distillation of the alcohol used [step (d)].

The reaction mixture is stirred for 1 to 4 hours at 120 to 150° C., in particular at about 135° C. to complete the reaction.

In another preferred embodiment of the present invention a pyridylcarboxylic amide of I or the salt I.1 thereof obtained according to the present invention is treated with an aromatic alcohol of formula V:

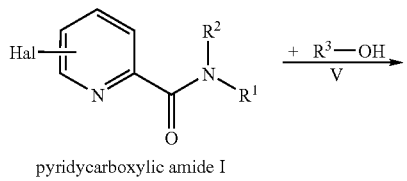

pyridycarboxylic amide I

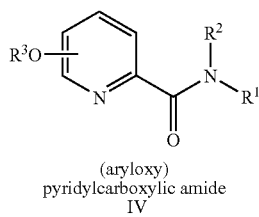

(aryloxy)
pyridylcarboxylic amide
IV

The reaction of the pyridylcarboxylic amides I or I.1 with an aromatic alcohol V is carried out at a temperature from 0° C. to 250° C., preferably at elevated temperatures from 60 to 200° C., in particular from 140 to 180° C., most preferred at 160° C.

Particular preference is given to a process according to the present invention wherein the pyridylcarboxylic amide of I or the salt thereof obtained according to the present invention is treated with an aromatic alcohol of formula V, wherein $R^3$ represents a phenyl group, which is substituted by one or more halogen atoms, nitro, cyano, $C_1$-$C_6$-alkyl, $C_1$-$C_6$-alkoxy or $C_1$-$C_6$-haloalkyl groups;

in particular a phenyl group which is substituted by $C_1$-$C_6$-haloalkyl;

preferred a phenyl group which is substituted by $C_1$-$C_4$-haloalkyl;

most preferred a phenyl group which is substituted by 3-trifluoro-methyl;

optionally in the presence of a base and an inert solvent.

In a particularly preferred embodiment according to this invention the solution of the pyridylcarboxylic amides 1, in particular N-(4-fluorophenyl)2-chloro-pyrid-6-ylin-ecarbox-amide, in a aromatic hydrocarbon solvent, is added to a mixture of a base, preferably a alkali hydroxide, in particular potassium hydroxide;

a polar aprotic solvent, in particular N,N-dimethylacetamide; and an aromatic alcohol of formula VII, in particular 3-hydroxybenzotrifluoride; at 100 to 140° C.

The resulting mixture is heated to temperatures from 140 to 200° C. and the aromatic hydrocarbon and water formed during the reaction is distilled off. Subsequently, the mixture is stirred at elevated temperatures for 1 to 4 hours. The solvent is distilled off under reduced pressure. The residue is diluted with an apolar solvent, in particular a mixture of aromatic and aliphatic hydrocarbons and washed with water or an aqueous alkali hydroxide. The aqueous phase is separated off and the organic phase is dried. The resulting crystals are collected by filtration, washed and dried at elevated temperatures and reduced pressure.

In order to facilitate a further understanding of the invention, the following illustrative examples are presented. The invention is not limited to the specific embodiments described or illustrated, but encompasses the full scope of the appended claims.

EXAMPLE 1

N-(4-fluorophenyl)2-chloro-pyrid-6-ylcarboxamide

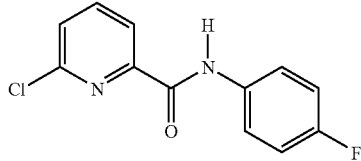

231 g (1 mol) molten 2-chloro-6-trichloromethylpyridin (=nitrapyrin =NP) is dosed to 98.1 g (1 mol) concentrated sulfuric acid (98% by weight) within 3 hours at 135° C. The resulting mixture is stirred for 3 hours at 135° C.

A viscous melted mass is formed which is added to a mixture of 122.0 g (1.1 mol) 4-fluoroaniline, 202.0 g (2 mol) triethylamine and toluene at temperatures between 20 and 100° C. within 45 minutes. The resulting reaction mixture is heated to temperatures between 80 and 120° C. and stirred for 1 hour. The mixture is treated with 500 ml of hydrochloric acid (7.5% by weight) at 80° C. and the phases are separated. The resulting solution of N-(4-fluorophenyl)2-chloro-pyrid-6-ylinecarboxamide in toluene is used for the preparation of N-(4-fluorophenyl)2-(3-trifluoromethyl-phenoxy)-pyrid-6-ylinecarboxamide (example 3) without further purification.

EXAMPLE 2

Isopropyl 2-chloro-pyrid-6-ylcarboxylate (CPAPE)

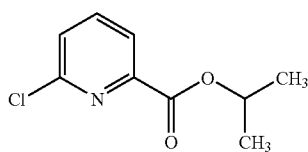

924 g (4 mol) molten NP is dosed to 510.2 g (5.2 mol) concentrated sulfuric acid (98% by weight), within 3 hours at 135° C. The resulting mixture is stirred for 3 hours at 135° C.

A viscous melted mass is obtained which is dosed to 2145 g (35.7 mol) isopropanol within 30 minutes starting at ambient temperature which raises to 60-65° C.

Remained isopropanol is distilled off under reduced pressure in 3 hours. The resulting product mixture is added to a mixture of xylene and water. Upon heating to 50° C. the organic phase is separated and washed with water. The obtained organic phase is dried and concentrated by distillation of xylene under reduced pressure.

The resulting product (2070 g) contains 34.1 wt % of isopropyl 2-chloro-pyrid-6-ylcarboxylate in xylene which corresponds to a yield of 88.4% based on NP and is used for the preparation of N-(4-fluorophenyl)2-(3-trifluoromethylphenoxy)-pyrid-6-ylinecarboxamide without further purification (examples 4 and 5).

EXAMPLE 3

N-(4-fluorophenyl)2-(3-trifluoromethylphenoxy)-pyrid-6-ylinecarboxamide

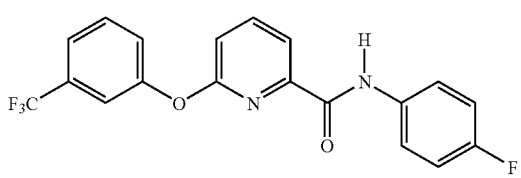

The solution of 13.5% (0.226 mol) N-(4-fluorophenyl)2-chloro-pyrid-6-ylinecarboxamide in toluene obtained according to example 1 is added to a mixture of 19.8 g (0.300 mol) potassium hydroxide, 47.1 g (0.291 mol) 3-hydroxybenzotrifluoride and 200 ml N,N-dimethylacetamide at 120° C. with stirring. The resulting mixture is heated to 160° C. and toluene and water formed during the reaction is distilled off. Subsequently, the mixture is stirred at 160° C. for two hours. The solvent is distilled off. The residue is diluted with xylene and isooctane and washed with water at 80° C. The aqueous phase is separated off and the organic phase is dried, diluted with isooctane and cooled down to 10° C. within 4 hours. The resulting crystals are collected by filtration and washed with isooctane and dried at 45° C. and 100 mbar. 73.2 g (0.195 mol) N-(4-fluorophenyl)2-(3-trifluoromethylphenoxy)-pyrid-6-ylinecarboxamide is obtained as a white solid with a purity of 97% representing an overall yield of 83.5% based on the amide obtained in example 2.

EXAMPLE 4

Isopropyl 2-(3-trifluoromethylphenoxy)-pyrid-6-ylinecarbonate

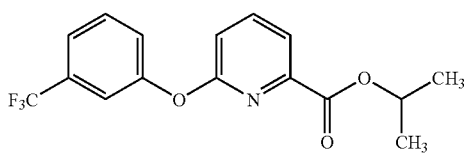

A 30% wt solution of 212.5 g sodium methoxide in methanol (1.22 equivalents NaOMe) is dosed in 1 h to a solution of 194.5 g (1.24 equivalents) 3-hydroxybenzotrifluoride in 856 g (8.31 equivalents) xylene at 120-110° C., with simultaneous distillation of methanol. The resulting phenolate mixture is slowly heated to 140° C. to distill off remained methanol.

A solution of 194.5 g (0.97 mol) isopropyl 2-chloro-pyrid-6-ylcarboxylate in xylene obtained from example 2 is dosed at 140° C. to the phenolate mixture in 30 min, followed by further heating and distillation of xylene to get a batch temperature of 150-155° C. which is kept for 4-6 h to complete the reaction. The resulting reaction mixture is cooled to 135° C. and directly used in example 5.

EXAMPLE 5

N-(4-fluorophenyl)2-(3-trifluoromethylphenoxy)-pyrid-6-ylinecarbox-amide

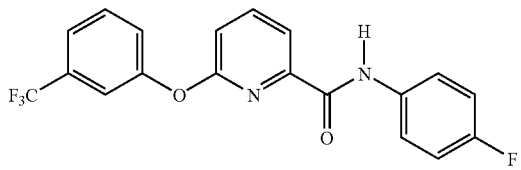

111.1 g (1.03 equivalents) 4-Fluoroaniline is added to the reaction mixture from example 4 at 135° C., followed by dosing in 30% wt solution of 24.3 g (0.13 equivalents) sodium methoxide in 30 min with simultaneous distillation of methanol. The reaction mixture is stirred for 2 h at 135° C. to complete the reaction. The reaction mixture is then added to a mixture of isooctane and water at 70° C., resulting in a final temperature of 80° C. The aqueous phase is separated off, the organic phase is washed with water at 80° C. The resulting product solution is dried azeotropically under Dean-Stark conditions to a final batch temperature of 105-110° C. The product solution is cooled to 5° C. in 5 h, including seeding at 68° C. The crystallized product is filtered, washed with isooctane and dried at 45° C. and 100 mbar.

316.5 g trifluoromethylphenoxy)-pyrid-6-ylinecarboxamide is obtained as a white solid with a purity of 99.3% representing an overall yield of 75.8% an NP.

What is claimed is:

1. A process for the preparation of a pyridylcarboxylic amide or ester I

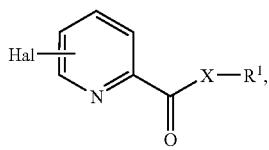

wherein

Hal represents a halogen atom;

X represents O or $NR^2$;

$R^1$ represents a $C_1$-$C_6$-alkyl or aryl group, wherein both groups may be substituted by one or more halogen atoms, nitro, cyano, $C_1$-$C_6$-alkyl, $C_1$-$C_6$-haloalkyl or $C_1$-$C_6$-alkoxy groups;

$R^2$ independently represents a hydrogen atom or a $C_1$-$C_6$-alkyl group;

which comprises:

(a) heating a mixture consisting essentially of a trichloromethylpyridine II,

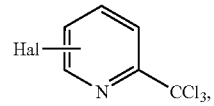

wherein Hal is a halogen atom, and 1.0 to 1.5 equivalents of concentrated sulfuric acid, wherein the trichloromethylpyridine II in a liquid form is added to the concentrated sulfuric acid at a temperature from 110° C. to 160° C.; and (b) reacting the intermediate product obtained in step (a) with an amine or alcohol III,

HXR$^1$, III, wherein X and $R^1$ have the meaning given above, optionally in the presence of a solvent, a base, or a combination thereof, wherein a pyridylcarboxylic amide or ester I is prepared.

2. The process of claim 1, wherein the trichloromethylpyridine II is represented by formula IIA

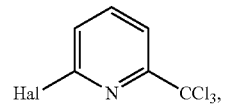

wherein Hal represents a halogen atom.

3. The process of claim 1, wherein

X represents O; and $R^1$ represents a $C_1$-$C_6$-alkyl group.

4. The process of claim 1, wherein

X represents $NR^2$;

$R^1$ represents a phenyl group which is substituted by one or two halogen atoms or $C_1$-$C_6$-haloalkyl groups; and $R^2$ represents a hydrogen atom.

5. The process of claim 1, wherein the trichloromethylpyridine II is added to the concentrated sulfuric acid at a temperature from 120 to 150° C.

6. The process of claim 1, wherein the mixture of the trichloromethylpyridine II and the concentrated sulfuric acid is kept at a temperature from 120 to 150° C. for 30 to 300 minutes.

7. The process of claim 1, wherein the sulfuric acid used contains less than 3% by weight of water.

8. The process of claim 1, wherein the intermediate product formed in step (a) is a compound of formula VI or VII or a structural isomeric form thereof,

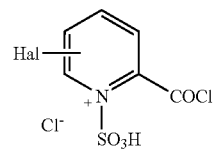

-continued

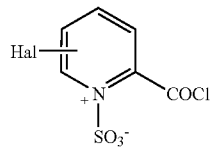
VII wherein Hal represents a halogen atom.

9. The process of claim 1, wherein the intermediate product formed in step (a) in a liquid form is added to the amine or alcohol III.

10. The process of claim 1, wherein the intermediate product obtained in step (a) is treated with an amine III in the presence of a base and an aromatic hydrocarbon as solvent.

11. The process of claim 1, further comprising treating a pyridylcarboxylic ester I, wherein X is O, with an amine III having the formula $HNR^1R^2$ in the presence of a base and an aromatic hydrocarbon as solvent.

12. A process for the preparation of an (aryloxy)pyridylcarboxylic amide or ester IV

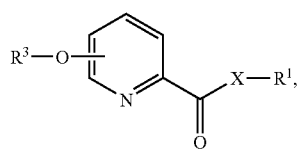
IV wherein
X represents O or $NR^2$;
$R^1$ represents a $C_1$-$C_6$-alkyl or aryl group, wherein both groups may be substituted by one or more halogen atoms, nitro, cyano, $C_1$-$C_6$-alkyl, $C_1$-$C_6$-haloalkyl or $C_1$-$C_6$-alkoxy groups;
$R^2$ represents a hydrogen atom or a $C_1$-$C_6$-alkyl group;
$R^3$ represents an aryl group, which may be substituted by one or more halogen atoms, nitro, cyano, $C_1$-$C_6$-alkyl, $C_1$-$C_6$-alkoxy or $C_1$-$C_6$-haloalkyl groups;
which comprises:
(a) heating a mixture consisting essentially of a trichloromethylpyridine II,

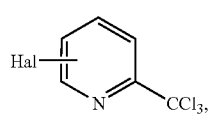
II wherein Hal is a halogen atom,
and 1.0 to 1.5 equivalents of concentrated sulfuric acid, wherein the trichloromethylpyridine II in a liquid form is added to the concentrated sulfuric acid at a temperature from 110 to 160° C.;
(b) reacting the intermediate product obtained in step (a) with an amine or alcohol III, $HXR^1$  III, wherein X and $R^1$ have the meaning given above, optionally in the presence of a solvent, a base, or a combination thereof; and (c) reacting the pyridylcarboxylic amide or ester I, or a salt thereof, obtained in step (b)

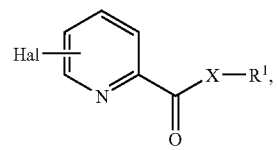
I with an aromatic alcohol V, $R^3$—OH  V, wherein $R^3$ has the meaning given above;
optionally in the presence of a base
wherein an (aryloxy)pyridylcarboxylic amide or ester IV is prepared.

13. The process of claim 12, wherein in step (c) the pyridylcarboxylic amide or ester I, or a salt thereof, is reacted with the aromatic alcohol V without further purification.

14. The process of claim 12, wherein in step (c) a pyridylcarboxylic ester IA,

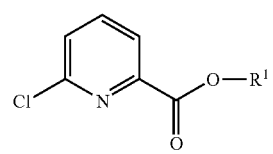
IA wherein $R^1$ represents a $C_1$-$C_6$-alkyl group,
is reacted with an aromatic alcohol V in the presence of a base.

15. The process of claim 12 wherein in step (c) a pyridylcarboxylic ester IA,

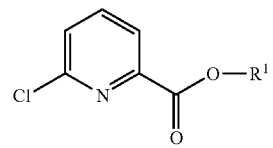
IA wherein $R^1$ represents a $C_1$-$C_6$-alkyl group,
is reacted with an aromatic alcohol V in the presence of a base, and further comprising
(d) treating the resulting (aryloxy)pyridylcarboxylic ester IV

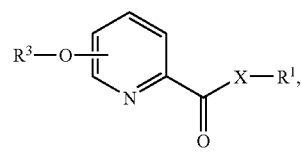
IV wherein X is O, with an amine III having the formula HNR$^1$R$^2$.

16. The process of claim 12 for the preparation of (aryloxy) pyridyl-carboxylic amides IV wherein R$^2$ is hydrogen, wherein step (c) comprises reacting a pyridylcarboxylic ester I with an amine III, wherein R$^2$ is hydrogen, and treating the resulting salt with an aromatic alcohol V.

* * * * *